United States Patent [19]

Chou

[11] 4,318,715
[45] Mar. 9, 1982

[54] PROCESS FOR SWEEPING METHANE FROM A PHYSICAL SOLVENT

[75] Inventor: Robert K. Chou, Parsippany, N.J.

[73] Assignee: Allied Corporation, Morris Township, Morris County, N.J.

[21] Appl. No.: 206,334

[22] Filed: Nov. 13, 1980

[51] Int. Cl.³ .............................................. B01D 45/00
[52] U.S. Cl. ......................................... 55/44; 55/53; 55/55; 55/73
[58] Field of Search ................... 55/23, 24, 25, 27, 38, 55/44, 55, 73, 53

[56] References Cited

U.S. PATENT DOCUMENTS

| | | | |
|---|---|---|---|
| 2,662,049 | 12/1953 | Magoa et al. | 55/44 X |
| 3,188,287 | 6/1965 | Hull | 55/44 |
| 3,518,056 | 6/1970 | Klett | 55/55 X |
| 3,594,985 | 7/1971 | Ameen | 55/44 |
| 4,080,424 | 3/1978 | Miller | 55/73 |

Primary Examiner—John Adee
Attorney, Agent, or Firm—Gerhard H. Fuchs; Ernest D. Buff

[57] ABSTRACT

The present invention provides a process for sweeping methane from a physical solvent used to remove carbon dioxide and hydrogen sulfide impurities from an impure methane stream. This process includes the steps of cocurrently mingling a mixture of physical solvent, methane, carbon dioxide and hydrogen sulfide with a flash gas to form a resulting gas and liquid mixture that has a higher concentration of carbon dioxide and a higher concentration of hydrogen sulfide than the liquid stream, and then flashing and separating the resulting stream at a pressure lower than the liquid feed pressure to yield a flash liquid that is further flashed at a pressure lower than the preceding flash pressure to provide the flash gas mingled with the feed liquid stream.

9 Claims, 5 Drawing Figures

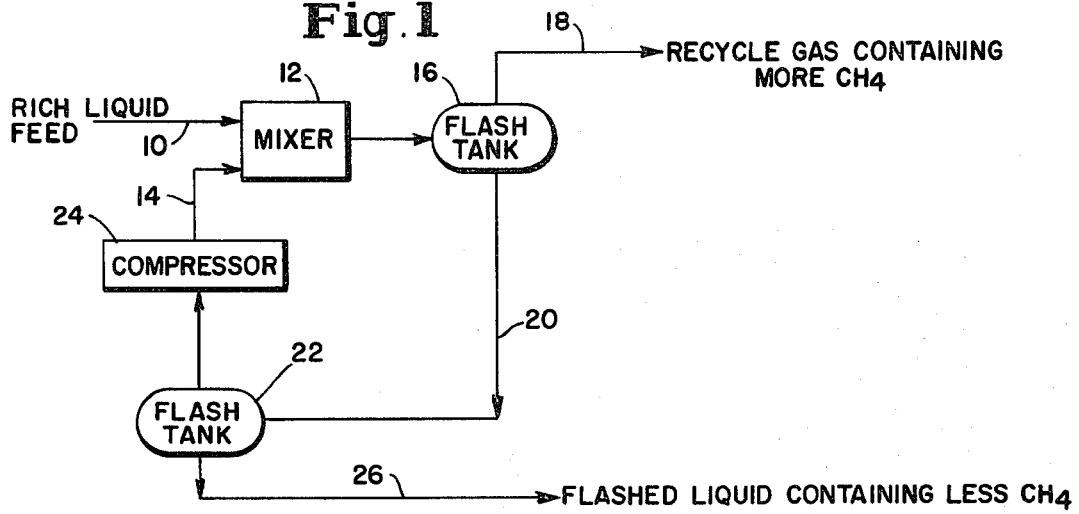
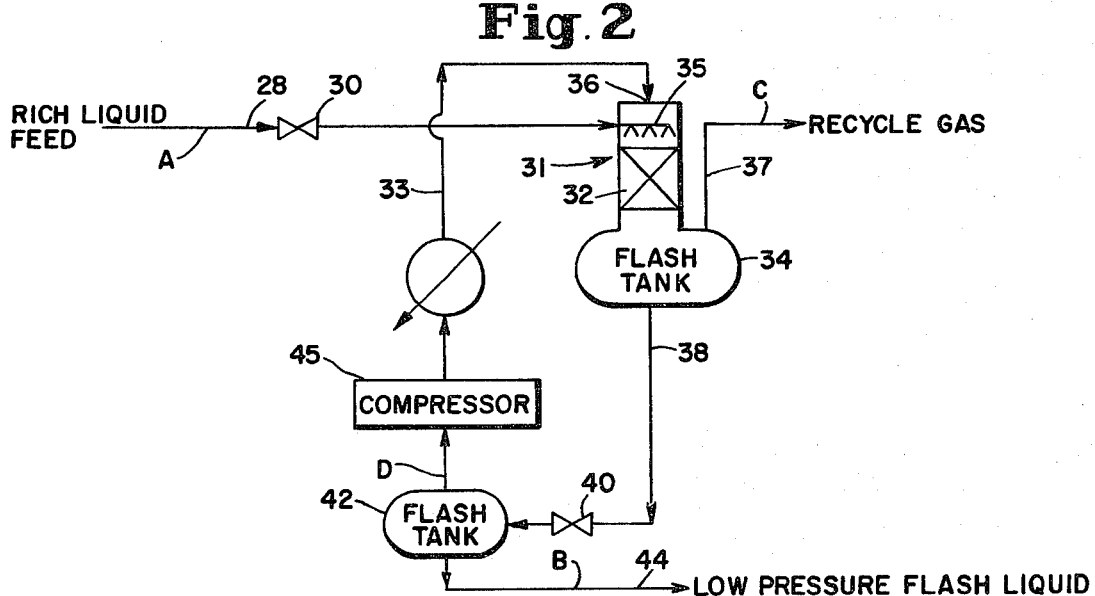
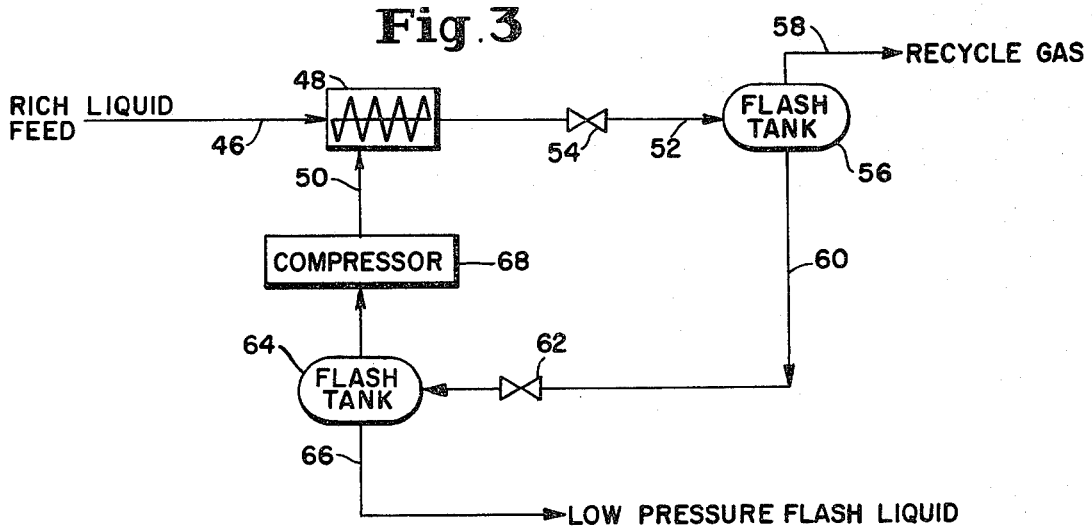

PROCESS FOR SWEEPING METHANE FROM A PHYSICAL SOLVENT

DESCRIPTION

Technical Field

This invention relates to the purification of an impure methane stream such as a low quality natural gas by an absorption process using a physical solvent, and particularly relates to sweeping methane from the physical solvent stream in which it is carried along, after the absorption step.

BACKGROUND ART

Mixtures of hydrogen sulfide with other gases, such as carbon dioxide and methane, are found in a number of industries. For example, mixtures of hydrogen sulfide, carbon dioxide, water and methane are found as natural gases. It is frequently necessary to remove hydrogen sulfide from gas mixtures for the purpose of purifying the gas mixture or recovering the hydrogen sulfide or both. For example, it is often necessary to purify a gaseous hydrocarbon stream to produce sweet, dry gas which will not poison certain catalysts and which will meet the usual pipeline specifications, and it is sometimes advantageous to recover the hydrogen sulfide as a source of elemental sulfur.

It is known in the prior art to absorb acid gas from an impure methane stream using a physical solvent in an absorber, to flash the acid gas-containing physical solvent stream at high pressure, to recycle the flashed gas to the absorber, to re-flash the flash liquid at low pressure, and to recycle the low pressure flash liquid to the absorber. Illustrative of this type of prior art is U.S. Pat. No. 3,594,985 to Ameen et al. It is also known in the prior art to flash the acid gas-containing physical solvent stream at intermediate pressure, to re-flash the flash liquid at low pressure and to combine the intermediate pressure and low pressure flash gases for recycling back to the absorber. Also known is a process using a tower having the intermediate third packed with rings and the upper and lower thirds as empty spaces, wherein an acid gas-containing physical solvent stream is flashed at intermediate pressure in the top third of the tower, the resulting flash liquid passes through the rings and out of the tower and is flashed at low pressure, and the low pressure flash gas is cycled into the bottom third of the tower for mixing with the intermediate pressure flash liquid.

All other prior art processes of which I am aware are deficient since they do not provide for optimum sweeping of the methane out of the acid gas-containing stream, do not provide an acid gas-containing stream with the proper concentration of carrying gas for the methane, do not provide a Claus gas for sulfur recovery that is very lean in methane, and do not provide a quantity of gas for recycling to the absorber that is less in volume but yet richer in methane, thus saving equipment cost and compression energy.

DISCLOSURE OF THE INVENTION

It is accordingly one object of the present invention to provide a process for optimizing the sweeping of methane out of an acid gas-containing physical solvent stream.

A further object of the present invention is to provide a process that makes provision for an acid gas-containing physical solvent stream with the proper concentration of carrying gas for the methane.

An even further object is to provide a Claus gas for sulfur recovery that is very lean in methane.

A still further object is to provide a quantity of gas for recycling to the absorber that is less in volume but yet richer in methane, thus saving equipment cost and compression energy.

Other objects and advantages of the present invention will become apparent as the description thereof proceeds.

In satisfaction of the foregoing objects and advantages there is provided by this invention a process for sweeping methane from a liquid composition containing methane, carbon dioxide, hydrogen sulfide and a physical solvent used to absorb carbon dioxide and hydrogen sulfide impurities from an impure methane stream. This process includes the steps of (a) cocurrently mingling the liquid composition with a first flash gas, the first flash gas produced at a first flash pressure, to form an intimately mixed stream having a higher concentration of each of carbon dioxide and hydrogen sulfide than the liquid composition; (b) flashing the intimately mixed stream at a second flash pressure to yield (1) a second flash gas, the second flash gas being richer in methane than the liquid composition, and (2) a flash liquid; and (c) flashing the flash liquid at the first flash pressure to produce the first flash gas and another flash liquid. The first flash pressure is lower than the second flash pressure, and the second flash pressure is lower than the feed pressure of the liquid composition.

BRIEF DESCRIPTION OF THE DRAWINGS

Reference is hereby made to the accompanying drawings which form a part of the specification of the present invention.

FIG. 1 broadly depicts the process of the present invention; and

FIGS. 2–5 are illustrative embodiments of the process of FIG. 1.

BEST MODE FOR CARRYING OUT THE INVENTION

Figure 4:
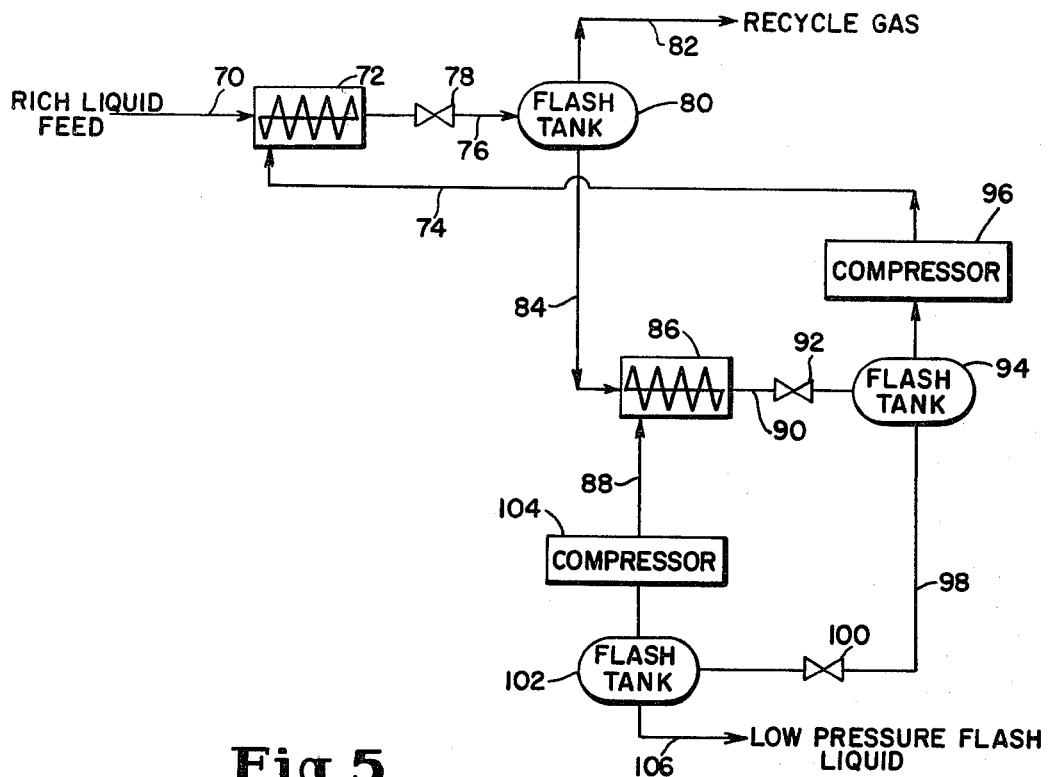

As discussed above, the present invention is concerned with a process for sweeping methane from a mixture of methane, carbon dioxide, hydrogen sulfide and a physical solvent used to remove carbon dioxide and hydrogen sulfide impurities from an impure methane stream. The impure methane stream is, for example, a low quality natural gas. Processes using a physical solvent to absorb carbon dioxide and hydrogen sulfide impurities from an impure methane stream and producing the mixture used as a starting material in the process of this invention are illustrated by U.S. Pat. No. 3,594,985 to Ameen et al, which is directed to separating acid gas, particularly hydrogen sulfide, from an impure natural gas stream, and U.S. Pat. No. 3,837,143 to Sutherland et al, which is directed to the simultaneous dehydration and sweetening of natural gas by removal of hydrogen sulfide and water.

The physical solvent used to absorb the carbon dioxide and hydrogen sulfide impurities in an absorption zone is any liquid that is capable of absorbing carbon dioxide and hydrogen sulfide impurities without chemical reaction, that has a high capacity to absorb these impurities, that is capable of easily desorbing these impurities and that is non-corroding. Exemplary physical solvents are dialkyl ethers of polyalkylene glycol, n- methyl-2-pyrrolidone, methanol and propylene carbonate, with dialkyl ethers of polyalkylene glycol being particularly suitable because of their non-toxic and non-polluting characteristics. When a dialkyl ether of a polyethylene glycol is selected as the physical solvent, it is preferably a dimethyl ether of polyethylene glycol and very preferably a mixture of dimethyl ethers of polyethylene glycols having 3 to 9 ethylene units, containing about 0 to 15% water, preferably from about 0.5 to 10% water by weight.

As explained above, the mixture of methane, carbon dioxide, hydrogen sulfide and physical solvent used as the starting material in the process of this invention is provided by contacting an impure methane stream containing carbon dioxide and hydrogen sulfide impurities with the physical solvent described above. The contacting step is suitably carried out in an absorption zone such as is provided by an absorber, and this mixture is thus an output stream from the absorber.

For purposes of this description of the invention, this absorber output stream is termed a feed stream and is more particularly called a rich liquid feed stream. In the first essential step of the process of the present invention, this feed stream is thoroughly mixed in cocurrent fashion with a flash gas produced in a later step. Mixing is carried out in any mixing device that provides good mixing and contacting between the feed stream and the flash gas. An exemplary mixer is a motionless mixer or spiral mixing vane, sometimes called a static mixing vane. The mixing may also be carried out in a tower or column containing a packing material such as rings. As a result of this mixing step, there is formed an intimately mixed stream having a higher concentration of each of carbon dioxide and hydrogen sulfide than the feed stream alone.

In the second essential step of this process, the stream formed by the mixing step is flashed at a pressure that is lower than the feed pressure of the rich liquid feed stream. Flashing is carried out adiabatically in a conventional flash tank to form a flash gas richer in methane than the feed stream, and to yield a flash liquid.

In the third essential step of this process, this flash liquid is flashed at a pressure lower than the pressure used in the previous flash step to produce the flash gas intimately mixed in the mixing step with the feed stream, and to produce another flash liquid. This flash liquid is very low in methane and useful to produce a Claus gas for sulfur recovery. The flash gas produced by this step may be later intermingled with the rich liquid feed for sweeping out most of the methane dissolved in the liquid. Flashing and separation is again carried out adiabatically in a conventional flash tank.

The hydrogen sulfide and carbon dioxide function as a carrying gas for the methane, that is, methane follows these acid gases. By providing a stream having the proper concentration of the carrying gas, the first flashing step produces a flash gas very much richer in methane than the feed stream. Furthermore, on a comparative basis, this flash gas is richer in methane than the combined stream produced by a typical procedure of the prior art for processing the feed stream and described in the comparative example set forth below. In this typical prior art procedure, the feed stream is flashed at a lower pressure than the feed pressure without mixing the stream with a flash gas, the resulting flash liquid is flashed at an even lower pressure, and the two flash gases are combined for recycling to the absorber.

As just explained, the process of the present invention provides a stream to be flashed that contains the proper concentration of carrying gas for the methane. Too much carrying gas dilutes the methane concentration and results in greater cost in terms of equipment and energy to recycle the methane, and too little carrying gas results in insufficient methane being flashed out. Between these two possibilities, there is an optimum concentration of carrying gas that results in the optimum concentration of methane being swept out.

The process of the present invention includes two stages being operated in series by mixing the flash liquid of the first flashing step with a flash gas produced by a later step to form a thoroughly mixed stream. Thus, when the second flashing step is carried out, the combined stream of the flash liquid and this flash gas is flashed. Mixing is carried out in an identical manner to the mixing step described above, and just as in that mixing step, the combined stream has a higher concentration of each of carbon dioxide and hydrogen sulfide than does the unmixed liquid stream. Accordingly, the flash gas produced by the second flashing step and cycled to the first mixing step, is richer in methane than the incoming liquid stream. When the second flashing step is carried out for the combined stream described above, there is produced a flash liquid, in addition to the flash gas just discussed. This flash liquid is flashed adiabatically in a conventional flash tank, at a pressure lower than the pressure of the second flashing step to form the flash gas that is combined in the second mixing step with the flash liquid from the first flashing step. Also formed is a flash liquid that is very low in methane and is beneficial for the preparation of Claus gas for sulfur recovery.

When the process of the present invention also includes two stages to be carried out in parallel, the flash liquid from the second flashing step is flashed adiabatically in a conventional flash tank at a pressure lower than that used in the second flash step to produce another flash liquid and another flash gas. In this case, the feed stream is mixed with the combination of this flash gas and the flash gas from the second flashing step. The flash liquid is very low in methane and is beneficial for the preparation of Claus gas for sulfur recovery.

As can be seen, in carrying out this process, the flash pressure is lower for each flash step, and the pressure at which the first flash step is carried out is lower than the feed pressure of the feed stream. The pressure drop is suitably provided by the use of conventional expansion valves or hydraulic turbines between flash tanks and before the first flash step. The pressures used in this process suitably range from about 150 kPa to about 10,000 kPa. The difference in pressure between successive flash steps could be very small but methane recovery would be less improved. Thus, a pressure difference between successive flash steps on the order of about 350–550 kPa is preferably minimal, with a greater difference of from about 1000 to 2000, even up to about 3500 kPa producing substantially greater methane sweeping. To illustrate, the feed pressure could be about 10,500 kPa, the pressure for the first flash step could be from about 3500 to 7000 kPa, and the pressure for the second flash step could be from about 700 to 2000 kPa. Also, for purposes of illustration, the feed pressure could be about 1900 to 2250 kPa, the pressure for the first flash step could be about 520 to 850 kPa, and the pressure for the second flash step could be from about 170 to 350 kPa. It is particularly suitable for the feed pressure to be from about 5500 to 8300 kPa, the pressure for the first flash step to be from about 2400 to 3400 kPa, and the pressure for the second flash step to be from about 700 to 1700 kPa.

The temperatures for the various liquid streams of this process range from about −20° C. to 140° C. Too far below −20 C., these streams will freeze, and too far above 140° C., these streams will not retain enough H$_2$S. However, it is preferred that the streams be from about −12° to 65° C. A temperature in the range of about −12° to 30° C. is particularly preferred. As a liquid stream progresses through the process, the stream temperature decreases several degrees each time the stream passes through an expansion valve or hydraulic turbine.

Reference is now made to FIG. 1 accompanying the application which broadly exemplifies the process of this invention. In this Figure, the rich liquid feed described above is fed by line 10 to mixer 12, in which the feed is mingled with a flash gas fed by line 14 to mixer 12. The flash gas is produced by a later flashing step. The intimately mixed stream passes from mixer 12 to flash tank 16, where it is flashed at a pressure lower than the feed pressure to yield a flash gas and a flash liquid. This flash gas exits by line 18 from tank 16, and the flash liquid is fed by line 20 to another flash tank 22, in which the liquid is flashed at a pressure lower than the pressure of the preceding flash step to form the flash gas mixed with the feed in mixer 12. This flash gas is driven by compressor 24 to mixer 12. Also formed is a flash liquid lean in methane that exits from tank 22 by line 26.

Reference is now made to FIGS. 2-5, which are illustrative embodiments of the process of FIG. 1. In FIG. 2, the rich liquid feed described above and at a high pressure is passed by line 28 through expansion valve 30 to scrubbing tower 31. Tower 31 contains a packing material 32 such as rings in order to provide for intimate mixing and contacting of the feed with a low pressure flash gas fed by line 33 to the tower. The bottom portion of tower 31 functions as flash tank 34. The feed is uniformly distributed over the top of the packing material by nozzles 35. The low pressure flash gas is fed into tower 31 at a point 36 above the nozzles. The low pressure flash gas and the feed intimately mix as they pass through packing material 32, and the resulting stream enters flash tank 34, where it is flashed at intermediate pressure to yield an intermediate pressure flash gas that exits the tank 34 by way of line 37, and yields an intermediate pressure flash liquid that passes from tank 34 by way of line 38 through expansion valve 40 to flash tank 42. The liquid is flashed in tank 42 to form a low pressure flash liquid that exits from tank 42 by way of line 44, and the low pressure flash gas which is fed by way of recycle compressor 45 to tower 31.

In FIG. 3, the rich liquid feed described above is fed at high pressure by line 46 to mixer 48. Mixer 48 is a motionless mixer or spiral mixing vane, sometimes called a static mixing vane, and may be any other mixing device that provides good mixing and contacting between the feed and a low pressure flash gas fed by line 50 to mixer 48. The intimately mixed stream is passed by line 52 to flash tank 56. Flashing of this stream in tank 56 at intermediate pressure yields an intermediate pressure flash gas that exits from tank 56 by way of line 58, and yields an intermediate pressure flash liquid that is fed from tank 56 by line 60 through expansion valve 62 to flash tank 64. Flashing of this liquid in tank 64 at low pressure produces a low pressure flash liquid which exits from tank 64 by way of line 66, and the low pressure flash gas, which is fed by way of compressor 68 back to mixer 48.

In FIG. 4, the process of the present invention is shown used in series. The rich liquid feed (designated steam A) described above is fed at high pressure by line 70 through expansion valve 78 to mixer 72. Mixer 72 is a motionless mixer or spiral mixing vane, and may be any other mixing device providing good contact between the feed and an intermediate pressure flash gas fed by line 74 to mixer 72. The intimately mixed stream is passed from mixer 72 by line 76 to flash tank 80. The stream is flashed at a high pressure that is lower than the feed pressure to form a high pressure flash gas (designated stream C) that exits from tank 80 by line 82, and a high pressure flash liquid (designated stream E) that is fed by line 84 from tank 80 through expansion valve 92 to mixer 86. Mixer 86 is a motionless mixer or spiral mixing vane, and may be any other mixing device providing good contact between the high pressure flash liquid and a low pressure flash gas (designated stream H) fed to mixer 86 by line 88. The resulting stream is fed from mixer 86 by line 90 to flash tank 94. In tank 94, the stream is flashed at intermediate pressure, and there is formed the intermediate pressure flash gas (designated stream G), which is fed by way of compressor 96 to mixer 72. Also formed in tank 94 is an intermediate pressure flash liquid (designated stream F) that is passed by line 98 through expansion valve 100 to flash tank 102. This liquid is flashed at low pressure in tank 102 to form the low pressure flash gas (designated stream H), which is fed from tank 102 by way of compressor 104 to mixer 86. There is also formed a low pressure flash liquid, (designated stream B), that exits from tank 102 by line 106.

Figure 5:
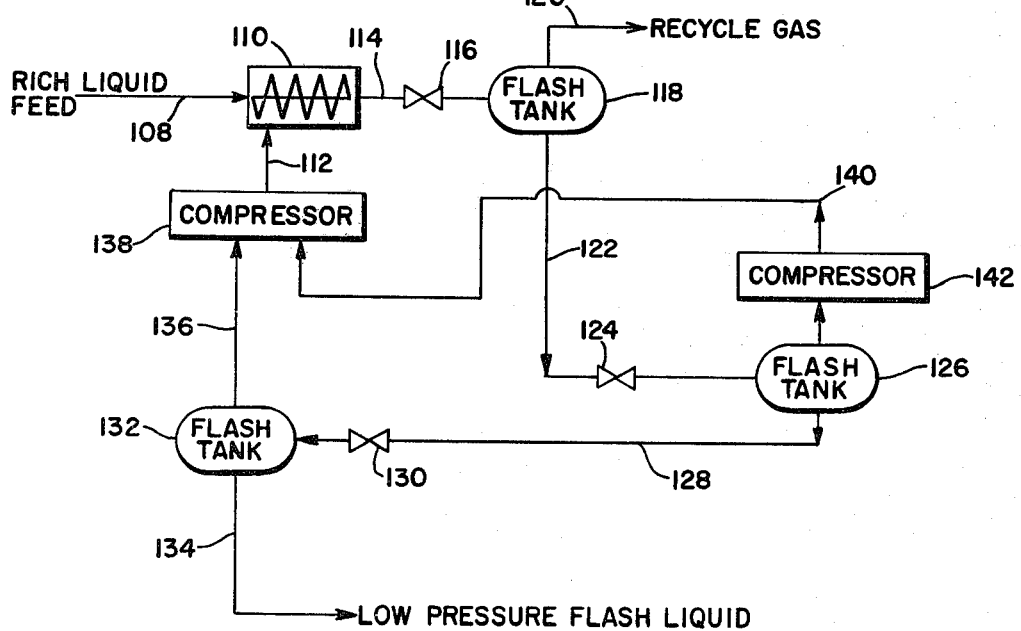

In FIG. 5, the process of the invention is shown used in parallel. The rich liquid feed described above (designated stream A) is fed by line 108 through expansion valve 116 at high pressure to mixer 110. Mixer 110 is a motionless mixer or spiral mixing vane, and may be any other mixing device that provides good contact between the feed and a flash gas (designated stream D), fed by lines 112 and 140 to mixer 110. The resulting stream is passed from mixer 110 by line 114 to flash tank 118. The stream is flashed at a high pressure that is lower than the feed pressure to form a high pressure flash gas (recycle gas, designated stream C) that exits from tank 118 through line 120, and high pressure flash liquid (designated stream E) that is fed from tank 118 by line 122 through expansion valve 124 to flash tank 126. The liquid is flashed at intermediate pressure to yield an intermediate pressure flash liquid (designated stream F) that is fed from tank 126 by line 128 through expansion valve 130 to flash tank 132. The liquid is flashed at low pressure to form a low pressure flash liquid (designated stream B) that exists from tank 132 by line 134, and a low pressure flash gas that is passed by line 136 by way of compressor 138 into line 112 joining together with the intermediate pressure flash gas from tank 126, which is passed by line 140 by way of compressor 142 to the point of junction with line 112.

The below-described comparative example illustrates prior art procedure with two flashing steps, wherein no methane sweeping action is used.

Examples 1 through 3, set forth below, further illustrate the present invention. The results of these Examples are compared to those obtained by prior art procedures illustrated by the Comparative Example. Examples 1 through 3 employ methane sweeping, in accordance with the invention, as follows: single sweep in Example 1; double sweep in series in Example 2; and double sweep in parallel in Example 3. All results are summarized in the Table below.

COMPARATIVE EXAMPLE

A rich liquid feed having composition "A" in the Table is fed from a simple absorption tower at 6895 kPa and 21° C. through an expansion valve into a flash tank. The temperature of the feed decreases 1° C. across the expansion valve. The feed is flashed in the flash tank at 2895 kPa to produce an intermediate pressure flash liquid that is passed by way of another expansion valve to another flash tank. The temperature of this liquid drops 2° C. in passing through this expansion valve. In this second flash tank, the liquid is flashed at 1172 kPa, and there is produced a low pressure flash liquid "B" and a low pressure flash gas (composition "D" in the Table). The low pressure flash gas is fed by way of a compressor to a point at which it junctions with the line by which the intermediate pressure flash gas is passed out of the first flash tank. The Table shows the composition of this combination of the intermediate pressure flash gas and low pressure flash gas as "C". This data shows that methane comprises only 49.5% of the combined intermediate pressure flash gas and low pressure flash gas.

Specific examples of the present invention will now be set forth. Unless otherwise indicated, the rich liquid feed is at ambient temperature. It is to be understood that these examples are merely illustrative, and are in no way to be interpreted as limiting the scope of the invention.

EXAMPLE 1

With reference to FIG. 2, a rich liquid feed having composition "A" in the Table is fed from a simple absorption tower at 6895 kPa and 21° C. through an expansion valve to a scrubbing tower packed with rings. The temperature of the feed drops 3° C. across the expansion valve. The feed is uniformly distributed over the top of the packing by the use of nozzles. A flash gas produced at a pressure of 1172 kPa by a later step is fed into the top of the tower at a location above the nozzles. The pressure of the flash gas is slightly greater than the 2896 kPa in the flash tank located at the bottom of the tower. The flash gas from compressor and feed liquid intimately mix in the tower as they pass through the rings. The resulting stream enters the flash tank beneath the tower where it is flashed and separated at 2896 kPa to form an intermediate pressure flash gas (composition "C" in the Table) and an intermediate pressure flash liquid. The intermediate pressure flash liquid passes from the flash tank through another expansion valve to another flash tank. The temperature of the liquid decreases 3° C. in passing through this expansion valve. The liquid is flashed in the tank at 1172 kPa to form the flash gas (composition "D" in the Table) initially fed to the tower by way of the recycle compressor. Also formed is a low pressure flash liquid that is passed out of the tank. The composition of the low pressure flash liquid "B" is set forth in the Table. As can be seen from this Table, the intermediate pressure flash gas contains 57.5% methane which is markedly richer in methane than that shown in the comparative case (49.5%). The low pressure flash liquid, stream B, is very suitable for producing Claus gas for sulfur recovery due to the very low methane content. As an associated benefit of this invention, the methane loss is less and compressor size and power for the recycle stream is smaller.

EXAMPLE 2

This example employs the invention process as illustrated by and as described, supra, with reference to FIG. 4, using two-stage sweeping actions in series. Stream A is the same rich liquid feed, but the low pressure flash liquid stream B contains even less methane, and the gas recycle stream C contains much higher methane (64.8%) due to two-stage sweeping actions in succession. This means less methane loss. Also, the recycle compressor and power can be smaller, because of lower recycle volume.

EXAMPLE 3

This example employs the invention process as illustrated by and as described, supra, with reference to FIG. 5 using two-stage sweeping actions in parallel. Stream A is the same rich liquid feed. As far as the Streams B and C are concerned, the performance and objective of this invention are same as that of Example 2.

TABLE (All data are in kilogram mole per hour)

| Comparative Example | Flash Without Sweeping Action | | | |
|---|---|---|---|---|
| Composition | A | B | C | D |
| $H_2S$ | 7,660 | 7,294 | 366 | 182 |
| $CO_2$ | 1,417 | 937 | 480 | 257 |
| $CH_4$ | 890 | 60 | 830 | 218 |
| $H_2O$ | 1,830 | 1,829.6 | 0.4 | 0.4 |
| *Selexol ® | 4,430 | 4,430 | 0 | 0 |
| | 16,227 | 14,550.6 | 1,676.4 | 657.4 |

| Example 1 | One Sweeping Action | | | |
|---|---|---|---|---|
| Composition | A | B | C | D |
| $H_2S$ | 7,660 | 7,399 | 264 | 204 |
| $CO_2$ | 1,417 | 1.060 | 357 | 323 |
| $CH_4$ | 890 | 52 | 838 | 214 |
| $H_2O$ | 1,830 | 1,829.6 | 0.4 | 0.4 |
| *Selexol ® | 4,430 | 4,430 | 0 | 0 |
| | 16,227 | 14,770.6 | 1,456.4 | 741.4 |

| Example 2 | Two Sweeping Actions In Series | | | |
|---|---|---|---|---|
| Composition | A | B | C | D |
| $H_2S$ | 7,660 | 7,466 | 194 | 164 |
| $CO_2$ | 1,417 | 1,162 | 255 | 228 |
| $CH_4$ | 890 | 47 | 843 | 348 |
| $H_2O$ | 1,830 | 1,822 | 8 | 0.6 |
| *Selexol ® | 4,430 | 4,430 | — | — |
| | 16,227 | 14,927 | 1,300 | 740.6 |

| Example 3 | Two Sweeping Actions In Parallel | | | |
|---|---|---|---|---|
| Composition | A | B | C | D |
| $H_2S$ | 7,660 | 7,460 | 200 | 231 |
| $CO_2$ | 1,417 | 1,135 | 282 | 350 |
| $CH_4$ | 890 | 47 | 843 | 340 |
| $H_2O$ | 1,830 | 1,821 | 9 | 0.4 |
| *Selexol ® | 4,430 | 4,430 | — | — |
| | 16,227 | 14,893 | 1,334 | 921.4 |

*Mixture of dimethyl ethers of polyethylene glycols having 3 to 9 ethylene units.

Industrial Applicability

The process has the advantage of producing a Claus gas for sulfur recovery that is very lean in methane. This process has the further advantage of improving methane recovery from a physical solvent used for absorbing acid gases from an impure methane stream.

The methane stream is illustratively a low quality natural gas.

I claim:

1. A process for sweeping methane from a liquid composition comprising methane, carbon dioxide, hydrogen sulfide and a physical solvent used to absorb carbon dioxide and hydrogen sulfide impurities from an impure methane stream, said processes comprising the steps of
   (a) cocurrently mingling said liquid composition with a first flash gas, said first flash gas produced at a first flash pressure, to form an intimately mixed stream having a higher concentration of each of carbon dioxide and hydrogen sulfide than said liquid composition;
   (b) flashing said intimately mixed stream at a second flash pressure to yield (1) a second flash gas, said second flash gas being enriched in methane, and (2) a flash liquid; and
   (c) flashing said flash liquid at said first flash pressure to produce said first flash gas and another flash liquid,
wherein said first flash pressure is lower than said second flash pressure, and said second flash pressure is lower than a feed pressure of said liquid composition.

2. The process of claim 1 further comprising the steps of
   (d) cocurrently mingling the flash liquid of step (b) with a third flash gas to form an intimately mixed combined stream having a higher concentration of each of carbon dioxide and hydrogen sulfide than said flash liquid, whereby the flash liquid of step (c) contains said third flash gas; and
   (e) flashing said another flash liquid of step (c) at a third flash pressure to form said third flash gas and an additional flash liquid;
wherein said third flash pressure is lower than said first flash pressure.

3. The process of claim 1 further comprising the steps of
   (d) flashing said another flash liquid of step (c) at a third flash pressure to produce an additional flash liquid and a third flash gas, wherein said first flash gas additionally contains said third flash gas when cocurrently mingled in step (a) with said liquid composition;
wherein said third flash pressure is lower than said first flash pressure.

4. The process of claim 1, wherein said first flash pressure, said second flash pressure and said feed pressure range from about 170 kPa to 10,500 kPa.

5. The process of claim 1, wherein said first flash pressure is from about 700 kPa to 1700 kPa, wherein said flash pressure is from about 2500 kPa to 34,000 kPa, and wherein said feed pressure is from about 5000 kPa to 8400 kPa.

6. The process of claim 1, wherein said physical solvent is a dialkyl ether of a polyalkylene glycol having 1 to 8 carbon atoms in each alkyl group and having 3 to 9 ethylene units.

7. The process of claim 6, wherein said physical solvent is a mixture of dimethyl ethers of polyethylene glycols having 3 to 9 ethylene units and containing about 0.5 to 15 weight percent water.

8. The process of claim 1, wherein said second flash gas is returned to an absorption zone.

9. The process of claim 1 wherein said another flash liquid is used as a feed material to produce Claus gas for sulfur recovery.

* * * * *

UNITED STATES PATENT AND TRADEMARK OFFICE
CERTIFICATE OF CORRECTION

PATENT NO. : 4,318,715
DATED : March 9, 1982
INVENTOR(S) : Robert K. Chou

It is certified that error appears in the above-identified patent and that said Letters Patent are hereby corrected as shown below:

Col. 5, line 7, "-20C" should read -- -20° C --.
Col. 8, line 40, in the Table "1.060" should read -- 1,060 --.
Col. 10, line 21, "said flash pressure" should read
       -- said second flash pressure --.

Signed and Sealed this

Twenty-fifth Day of May 1982

[SEAL]

Attest:

Attesting Officer

GERALD J. MOSSINGHOFF

Commissioner of Patents and Trademarks